US010744308B2

(12) United States Patent
Chen et al.

(10) Patent No.: US 10,744,308 B2
(45) Date of Patent: Aug. 18, 2020

(54) LOW-PROFILE VENTRICULOAMNIOTIC SHUNT FOR FETAL AQUEDUCTAL STENOSIS

(71) Applicant: UNIVERSITY OF PITTSBURGH-OF THE COMMONWEALTH SYSTEM OF HIGHER EDUCATION, Pittsburgh, PA (US)

(72) Inventors: Yanfei Chen, Pittsburgh, PA (US); Young Jae Chun, Pittsburgh, PA (US); Stephen Emery, Pittsburgh, PA (US); Xinzhu Gu, Jefferson Hills, PA (US); William Wagner, Gibsonia, PA (US); Stephanie Greene, Glenshaw, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 316 days.

(21) Appl. No.: 15/765,723

(22) PCT Filed: Oct. 13, 2016

(86) PCT No.: PCT/US2016/056751
§ 371 (c)(1),
(2) Date: Apr. 4, 2018

(87) PCT Pub. No.: WO2017/066389
PCT Pub. Date: Apr. 20, 2017

(65) Prior Publication Data
US 2018/0296810 A1    Oct. 18, 2018

Related U.S. Application Data

(60) Provisional application No. 62/241,281, filed on Oct. 14, 2015.

(51) Int. Cl.
*A61M 27/00* (2006.01)
*A61M 25/00* (2006.01)
(Continued)

(52) U.S. Cl.
CPC .......... *A61M 27/006* (2013.01); *A61M 25/00* (2013.01); *A61M 27/00* (2013.01);
(Continued)

(58) Field of Classification Search
CPC ...... A61M 2205/0266; A61M 2207/00; A61M 25/00; A61M 27/00; A61M 27/006; A61M 39/24
(Continued)

(56) References Cited

U.S. PATENT DOCUMENTS 3,894,541 A    7/1975    El-Shafei
4,474,569 A    10/1984   Newkirk
(Continued)

*Primary Examiner* — Leslie R Deak
(74) *Attorney, Agent, or Firm* — Eckert Seamans Cherin & Mellott, LLC; Carol A. Marmo

(57) ABSTRACT

The invention relates to an in-utero ventriculoamniotic shunting device that includes a shunt tube (26) composed of polymer composite and having metallic wire embedded therein, one or more anchors (30) composed of superelastic wire, e.g., thermal shape-set nitinol structures, that are mechanically attached to an exterior surface of the shunt tube (26), and a one-way passive valve (32) composed of a thin polymer membrane. The anchors (30) are effective to prevent migration and dislodgement of the shunting device following its deployment, and the valve (32) is effective to prevent the backflow of amniotic fluid (23).

12 Claims, 5 Drawing Sheets

(51) Int. Cl.
*A61M 39/24* (2006.01)
*A61B 5/00* (2006.01)
*A61B 5/03* (2006.01)
*A61B 5/055* (2006.01)
*A61L 31/12* (2006.01)

(52) U.S. Cl.
CPC .......... *A61M 39/24* (2013.01); *A61B 5/031* (2013.01); *A61B 5/055* (2013.01); *A61B 5/4362* (2013.01); *A61L 31/128* (2013.01); *A61M 2205/0266* (2013.01); *A61M 2207/00* (2013.01)

(58) Field of Classification Search
USPC ........................................................ 604/8–9
See application file for complete search history.

(56) References Cited

U.S. PATENT DOCUMENTS

| | | |
|---|---|---|
| 4,475,898 A | 10/1984 | Brodner et al. |
| 2003/0220604 A1 | 11/2003 | Al-Anazi |
| 2006/0224101 A1 | 10/2006 | Glenn |

LOW-PROFILE VENTRICULOAMNIOTIC SHUNT FOR FETAL AQUEDUCTAL STENOSIS

CROSS-REFERENCE TO RELATED APPLICATION

This application is a U.S. National Stage Application under 35 U.S.C. § 371 of International Application No. PCT/2016/056751, filed on Oct. 13, 2016, which claims priority under 35 U.S.C. § 119(e) from U.S. Provisional Patent Application No. 62/241,281, filed on Oct. 14, 2015, both of which are entitled "A NOVEL LOW-PROFILE VENTRICULOAMNIOTIC SHUNT FOR FETAL AQUEDUCTAL STENOSIS," the contents of which are incorporated herein by reference.

FIELD OF THE INVENTION

The invention relates to a ventriculoamniotic device, e.g., shunt, for in-utero implantation to treat fetal aqueductal stenosis.

BACKGROUND

Hydrocephalus is defined as a clinical entity in which a disturbance of cerebrospinal fluid (CSF) circulation causes the accumulation of intraventricular CSF, resulting in progressive ventricular dilation. It can be divided as two groups: hydrocephalus seen in early life and hydrocephalus seen in adults based on the time of onset. In the early life hydrocephalus group, fetal hydrocephalus is of significant concern since children with an obvious prenatal onset of hydrocephalus have been found to be at high risk for early death or multiple neurological impairments. It is reported that fetal hydrocephalus occurs at an estimated rate of 0.2-1 per 1,000 deliveries and the prevalence varies due to the various or obscure definitions of congenital hydrocephalus. Fetal pressure hydrocephalus due to obstruction of flow of fluid through and then out of the ventricular system damages the developing brain. Neurologic consequences are devastating and permanent.

Aqueductal stenosis (AS) is a unique neurodevelopmental anomaly that causes pressure hydrocephalus by obstruction of the aqueduct of Sylvius, which is the narrowest portion of the central nervous system (CNS) ventricular system between the third and fourth ventricles. It is fundamentally different from other causes of hydrocephalus that result from a malformation, deformation, or disruption of the developing brain. Fetuses with AS, usually have otherwise normal brains. Neurologic injury in AS is the result of pressure on the developing neurons. It therefore stands to reason that fetuses with AS may benefit from decompression of the ventricular system, thereby arresting brain injury and preventing ongoing damage.

In-utero shunting of CSF from the ventricles to the amniotic fluid was attempted in the early 1980s as a means of improving pregnancy outcomes. The ventriculoamniotic shunts were, in general, simple silastic tubes with a one-way valve to prevent amniotic fluid from refluxing into the ventricles. They were placed by ultrasound guidance through a large bore needle. They had a tendency to clog. In addition, they had a tendency to migrate since there was no effective means for anchoring the device to prevent dislodgement. Intrauterine treatment was shown to be technically feasible. Shunting was abandoned, however, in the mid-1980s due to a perceived lack of effect. In retrospect, the lack of effect was likely due to poor patient selection and technical difficulties as a consequence of technological limitations of the day. Because of the inability to accurately assess fetal neuroanatomy in the 1980s, shunts were placed in fetuses with lesions other than AS. Not surprisingly, analysis of the data on pregnancy outcomes after shunting showed no clear benefit. A moratorium was placed on fetal ventriculoamniotic shunting in the mid-1980s and since, there has been almost no progress in treatment of fetal hydrocephalus and ventriculoamniotic shunts are not commercially available.

Prenatal ventricular decompression is currently not a management option for fetal pressure hydrocephalus. Current management for fetal hydrocephalus involves either preterm delivery followed by postnatal shunting or expectant management to term and then shunting. Problems associated with early delivery are concomitant prematurity, poor surgical candidacy, and a greater rate of shunt complications. Problems associated with expectant management are ongoing brain injury and obstetric complications related to macrocephaly (excessively large fetal head), which can impact the current as well as future pregnancies due to the need for cesarean delivery. The type of cesarean section typically required is a "classical," or vertical uterine incision which is subject to rupture in subsequent pregnancies, placing both mother and fetus at risk for death or disability. This represents an unfavorable risk-benefit assessment as the mother is exposed to significant risk, but the newborn may not receive benefit since neurologic damage is typically complete by term.

Thus, there is a need to address these issues by identifying an appropriate patient population for ventriculoamniotic shunting, i.e., isolated AS, through prenatal detection devices and methods including ultrasound and MRI techniques and, designing and developing in-utero shunting devices and methods for arresting brain injury and allowing the pregnancy to proceed to term, after which standard ventriculoperitoneal shunting can be performed in the newborn period. Neurologic function is potentially preserved while the pregnancy progresses to term. Term newborns are superior surgical candidates as compared to preterm infants.

SUMMARY OF THE INVENTION

The invention provides an in-utero ventriculoamniotic shunting device that includes a shunt tube, one or more anchors and a one-way passive valve. The shunt tube includes an exterior surface, a first end, an opposite second end, a length, an inner diameter, an outer diameter and a composite that forms the inner diameter and the outer diameter. The composite includes one or more polymer layers, and metallic wire embedded in the one or more polymer layers. The one or more anchors are mechanically attached to the exterior surface of the shunt tube and include nitinol wire configured in a shape that extends outwardly from the exterior surface of the shunt tube to prevent migration of the shunting device, and a mechanism to connect the nitinol wire to the exterior surface of the shunt tube. The one-way passive valve includes a membrane cover mechanically connected to a portion of a perimeter of the opposite second end of the shunt tube in a hinge-like configuration.

The length of the shunt tube can be from about 2 to about 10 cm. The inner diameter of the shunt tube can be from about 0.5 to about 1.5 mm. The outer diameter of the shunt tube can be from about 1.0 to about 3.0 mm.

In certain embodiments, the nitinol wire is configured in the shape of a coil having a plurality of spirals formed on the exterior surface and wrapped around the outer diameter of the shunt tube. In certain other embodiments, the nitinol wire is configured in the shape of two curves extending outwardly from the exterior surface of the shunt tube.

The one or more anchors can be mechanically attached to the outside surface of the shunt tube at a position approximately mid-point on the length of the tube. The one or more anchors can have a length of about 1 to about 4 cm.

The valve may be composed of a thin polymeric membrane. In certain embodiments, the valve includes poly(ester urethane) urea. The poly(ester urethane) urea can be fabricated by electrospinning.

In another aspect, the invention provides a method of ventriculoamniotic shunting for fetal isolated aqueductal stenosis. The method includes prenatally detecting and diagnosing aqueductal stenosis in a fetus; forming a shunting device, which includes obtaining a shunt tube, which has an exterior surface, a first end having an opening, an opposite second end having an opening, a length, an inner diameter, an outer diameter, a composite that forms the inner diameter and the outer diameter, wherein the composite includes one or more polymer layers and metallic wire embedded in the one or more polymer layers; mechanically attaching one or more anchors to the exterior surface of the shunt tube, which include fabricating nitinol wire; thermally configuring the nitinol wire in a shape that extends outwardly from the exterior surface of the shunt tube for preventing migration of the shunting device; and employing a mechanism for connecting the nitinol wire to the exterior surface of the shunt tube; and mechanically attaching a membrane cover to a portion of a perimeter of the opposite second end of the shunt tube in a hinge-like configuration; introducing the shunting device in-utero through a skull and into a brain of the fetus, such that the first end of the shunt tube is positioned in the skull and the opposite second end of the shunt tube is positioned in an amniotic sac outside of the skull; allowing cerebrospinal fluid in the brain to flow into the first end and through the shunt tube; pushing outward the membrane cover by the flow of cerebrospinal fluid through the shunt tube; and discharging the cerebrospinal fluid through the opposite second end of the tube into the amniotic sac.

BRIEF DESCRIPTION OF DRAWINGS

A full understanding of the disclosed concept can be gained from the following description of the preferred embodiments when read in conjunction with the accompanying drawings, in which.

DETAILED DESCRIPTION OF THE PREFERRED EMBODIMENTS

The invention relates to devices and methods for identifying an appropriate patient population for ventriculoamniotic shunting, i.e., isolated AS, through detection devices and methods prenatally using both ultrasound and MRI techniques and, designing and developing in-utero shunting devices and methods for arresting brain injury and allowing the pregnancy to proceed to term. The invention includes novel low-profile ventriculoamniotic shunting devices with an anchor and a one-way valve to relieve high intracranial pressure. The devices' functionality includes one or more of the following: relieving high intracranial pressure and, preventing device dislocation and inhibiting reflux of cerebrospinal fluid (CSF). The objectives of the devices and methods of the invention include arresting brain injury, preventing further damage, preserving neurologic function, and allowing for normal development thereby avoiding life-long suffering of affected children and the associated medical, emotional and financial burden of the disease.

In accordance with the invention, the ventriculoamniotic shunting devices are composed of composites containing multiple polymer layers with ultra-thin braided metal wires. The ventriculoamniotic shunting devices include a tube e.g., catheter, that has embedded therein metallic wire. The tube is composed of a soft material, e.g., polymer, which is biocompatible, longitudinally flexible, as well as resistant to buckling and kinking. There are a wide variety of biocompatible polymers that are known in the art and suitable for use in constructing the tube e.g., catheter. Non-limiting examples of suitable materials include two different types of catheter materials, e.g., 3 Fr and 4 Fr size tubes, which are commercially available by mechanical cut-trim process from Neuroform3 Microdelivery Stent System (Boston Scientific, MA) and the Angiographic Catheter (SRD6913, Cordis, Johnson & Johnson Co., FL), respectively. These commercially available catheter materials are commonly used in either neurovascular or coronary artery interventional procedures.

The dimensions of the tube can vary. In certain embodiments, the outer diameter can be in a range from about 1.0 mm to about 3.0 mm, such as, but not limited to about 1.0 mm or about 3.0 mm. The inside diameter can be in a range from about 0.5 mm to about 1.5 mm, such as, but not limited to about 0.6 mm or about 1.4 mm. The length of the tube can also vary and in certain embodiments, is from about 2 cm to about 10 cm, such as, but not limited to about 7 cm.

Figure 1A:
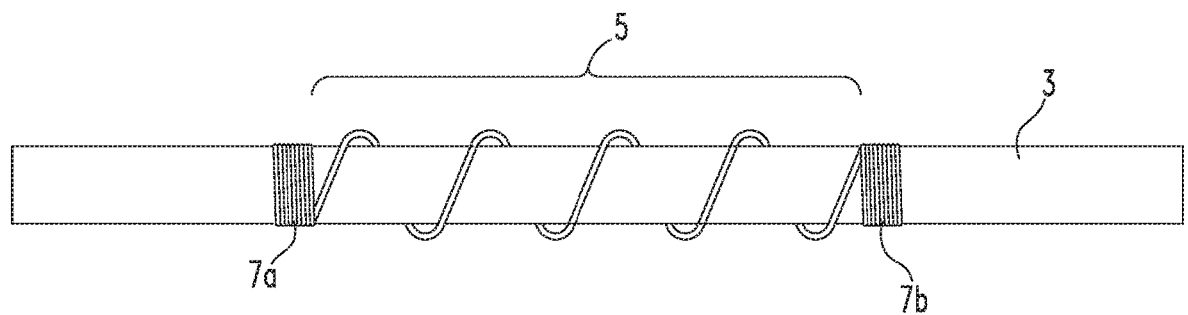
FIGS. 1A, 1B and 1C are schematics that show anchor designs in accordance with certain embodiments of the invention.
Figure 1B:
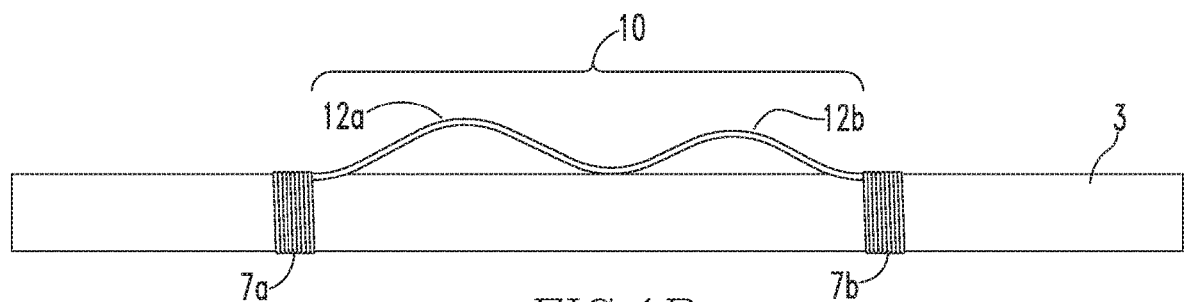
Figure 1C:
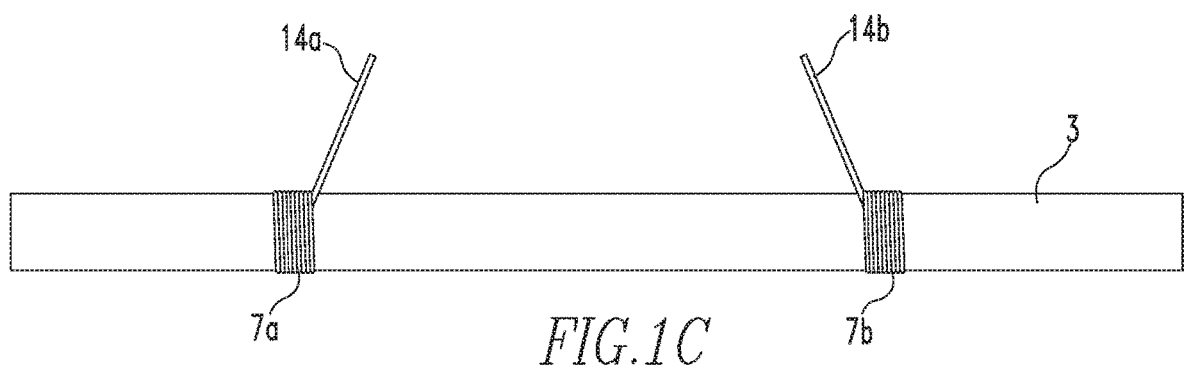

One or more anchors are attached to the outer surface of the tube. The design of the anchors can vary and suitable designs include, but are not limited to, coiled and braided wire structures. For example, the length of the anchors can vary and in certain embodiments, can be from about 1 to about 4 cm. The anchors are positioned along a portion of the length of the tube. In certain embodiments, one or more anchors may be positioned in substantially the middle of the tube, e.g., midpoint of the tube length. In other embodiments, one anchor may be positioned near one end of the tube and another anchor may be positioned near another, opposite end of the tube. The anchors are mechanically attached on the tube after pre-shape setting of the wires. FIGS. 1A, 1B and 1C are schematics that show suitable anchor designs in accordance with certain embodiments of the invention. FIG. 1A includes a neurovascular catheter 3, and a wire anchor 5 that is coiled around a middle portion of an outer surface of the catheter 3. At one end of the wire anchor 5 is a first suture 7a and at another opposite end of the wire anchor 5 is a second suture 7b, which are operable to connect/attach the wire anchor 5 to the catheter 3. It is contemplated and understood that the number of spirals in the coiled anchor 5 can vary and the length of the anchor 5 can also vary. FIG. 1B shows the catheter 3 and sutures 7a and 7b, as shown in FIG. 1A. However, in FIG. 1B there is a wire anchor 10 that extends in the middle portion of the catheter 3 between the sutures 7a and 7b, which includes two curves 12a and 12b, e.g., "bumpers", extending outwardly from the outer surface of the catheter 3. FIG. 1C shows the catheter 3 and sutures 7a and 7b as shown in FIG. 1A. However, in FIG. 1C, there are two wire anchors 14a, 14b, each of which is connected/attached to the surface of the catheter 3 by the sutures 7a and 7b, respectively. Anchor 14a slants or tilts and extends outwardly in a direction toward 14b and vice versa. It is contemplated and understood that the shape of the wire anchor can vary widely and is not limited by the designs and shapes illustrated herein. Generally, any anchor design or shape may be used provided that it precludes displacement of the tube when placed in-utero. Thus, suitable designs and shapes include those that are effective to prevent migration and dislodgement of the shunting device after its deployment.

There are a variety of materials that are known for use as wire in implantable biomedical devices, and that are suitable for use in the invention. In particular, nitinol wires are suitable for use in fabricating the anchors for the ventriculoamniotic shunt devices, in accordance with the invention. Nitinol is a common and well-known material widely used for implantable biomedical devices because of its shape memory effect, superelasticity and biocompatibility. The use of nitinol in a medical device allows for the efficient deployment in a less invasive procedure with its superelastic attribute, e.g., superelastic nitinol at body temperature allows for self-expanding deployment. Most vascular disease treatment procedures require instruments and devices that can pass through very small openings and then elastically spring back into desired shapes. Nitinol clearly allows vast freedom in design as compared to other flexible materials. As for biocompatibility, it has been found in the art that almost no toxic effects or decrease in cell proliferation is associated with nitinol, as well as no inhibiting effect on the growth of cells in contact with its surface.

Non-limiting examples of suitable nitinol wires for fabricating anchors include cold-drawn superelastic nitinol wires, which are commercially available from Nitinol Devices & Components, Inc., CA. The elastic moduli of these wires are in the range of 41 to 75 GPa with an ultimate tensile strength of 1070 MPa. The transformation temperature (i.e., Austenite finish temperature) is in a range between −25 and 30° C. The composition includes 55.8 wt. % nickel and 44.2 wt. % titanium.

The nitinol wires can be fabricated into the structures shown in FIGS. 1A, 1B and 1C, or alternatively, can be formed into other anchor designs. In certain embodiments, as shown in FIG. 1A, a coil structured anchor 5 design includes a spring-like shaped superelastic nitinol wire attached on the outer surface of the tube. Further, as shown in FIG. 1B, a two-bumper structured anchor 10 design has two curved shapes along the tube.

The nitinol wire anchors are covered to provide a continuous conduit for fluid flow. The cover material can consist of thin film metallic or polymer layers, such as, thin layers of nitinol membrane, ePTFE, Dacron polyester, as well as electrospun fibers using polyurethane (PU) or poly(ester urethane) urea (PEUU), and mixtures and combinations thereof.

The device further includes a valve, e.g., a one-way valve, that is designed, manufactured and attached to an end of the tube to prevent any backflow of amniotic fluid into the fetal brain. In certain embodiments, the one-way valve includes biomimetic bi- or tri-leaflets (similar to cardiac or venous valves). The valve permits maximum fluid flow when opened, and provides a low profile structure because of the use of thin elastic membranes. In certain embodiments, a simple, low-profile, one-way valve includes covering one end of the tube, e.g., catheter, with poly(ether urethane) urea membrane (about 200 μm thick). The membrane is attached along a portion of the perimeter of the tube end. The membrane is not attached along the entire perimeter of the tube end, such as not to completely seal the opening of the tube. Thus, the partial attachment along the perimeter provides for a hinge-like configuration, which automatically opens to allow fluid to flow out of the tube and automatically closes to preclude back flow into the tube.

The valve can be composed of various materials, such as, polymeric membrane, that is known in the art. Preferable materials include those that have a degree of elasticity (e.g., when used in accordance with the invention, capable of resisting forward and back flow). The elasticity of the material is a consideration and may be important because the device typically will be partially attached to function in a hinge-like manner without the use of an actual hinge. Non-limiting examples include, but are not limited to, poly(ester urethane) urea, poly(ether urethane) urea (as above-described), and combinations and mixtures thereof. Properties of the polymeric membrane may be tailored or customized during fabricating the material using electrospinning techniques.

Poly(ester urethane) ureas (PEUU) have been shown to possess good biocompatibility with non-toxic degradation and exceptional elastomeric properties.

There are various methods known in the art for preparing PEUU. In certain embodiments, PEUU can be prepared by a two-step polymerization process whereby polycaprolactone diol, 1,4-diisocyanatobutane, and 1,4-diaminobutane are combined in a 1:2:1 molar ratio. In the first step, a pre-polymer is formed by reacting polycaprolactone diol with 1,4-diisocyanatobutane. In the second step, the pre-polymer is reacted with 1,4-diaminobutane to extend the chain and to form the final polymer.

The PEUU for use in coating the nitinol wire anchors, and for use in constructing the valve, can be fabricated by electrospinning. In certain embodiments, PEUU is dissolved in 1,1,1,3,3,3-hexafluoroisopropanol (HFIP) at a concentration of 12% (w/v), and electrospun either directly onto the superelastic nitinol anchor to achieve a thin layer or coating, or onto a rotating and translating stainless steel mandrel to yield a PEUU membrane. The deposition parameters and conditions may vary and, in certain embodiments, may include feeding the PEUU solution through a charged capillary at a rate of about 1.5 ml/h, locating the collecting target (nitinol anchor or rotating mandrel) about 10 cm from the tip of the capillary, and providing voltage between the capillary and target of about 19 kV.

In an embodiment of the invention, a buckling-resistant, soft polymer composite tube having spiral metallic wire embedded therein is used, which is commercially available as 3 Fr neurovascular catheter from Boston Scientific. In this embodiment, the tube has an outer diameter of about 1.0 mm and an inner diameter of about 0.6 mm. Two anchors are mechanically attached to the outer surface of the tube. Each of the anchors consists of a superelastic 3 um-braided cylindrical nitinol wire structure. The two anchors are positioned substantially at the midpoint of the length of the tube. As mentioned herein, in accordance with the invention, it is understood that various anchor designs can be used.

Figure 2:
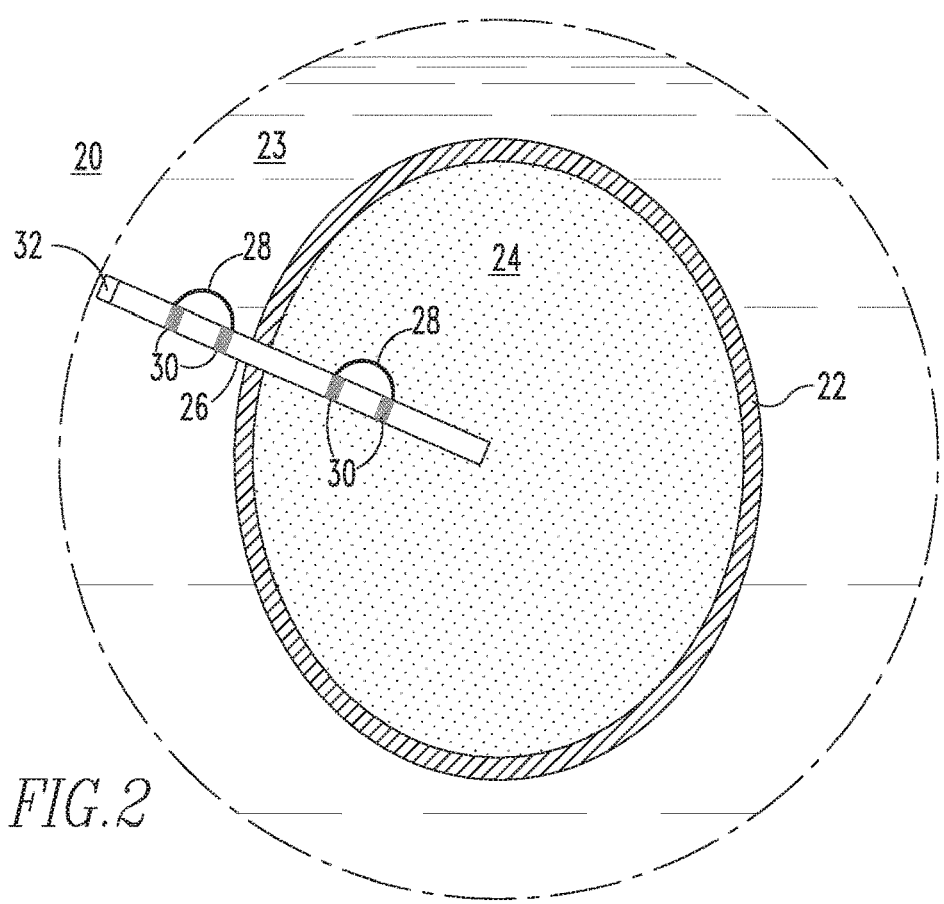
FIG. 2 is a schematic that shows a ventriculoamniotic shunt device implanted in a fetal brain, in accordance with certain embodiments of the invention.

FIG. 2 is a schematic of a ventriculoamniotic shunt system 20 implanted in a fetal brain, in accordance with certain embodiments of the invention. FIG. 2 includes a fetal skull 22 that houses a fetal brain 24. A catheter tube 26 is introduced through the skull 22 into the brain 24, such that one, e.g., proximate, end of the tube 26 is positioned inside the skull 22 and an opposite, e.g., distal, end of the tube 26 is located outside the skull 22 in the amniotic sac 23. The tube 26 serves as a conduit to drain excessive CSF from the brain 24 to the amniotic sac 23. The tube 26, as shown in FIG. 2, has two anchors 28, e.g., thermal-shaped nitinol wires, attached to an outer surface of the tube 26 using sutures 30, to prevent dislocation of the tube 26. One anchor is positioned within the skull 22 and the other anchor is positioned outside of the skull 22. The proximate end of the tube 26 that is positioned within the skull 22 and brain 24, is open to allow fluid to enter the proximate end of the tube 26 and flow therethrough. The distal end of the tube 26 that is located outside the skull 22, has a one-way valve 32 partially fixed along a perimeter of the distal end of the tube 26. Thus, excessive CSF enters the proximate end, flows through the tube 26, pushes the valve 32 into its open configuration, and exits into the amniotic sac 23. When there is no excessive CSF flowing through the tube 26, the valve 32 is in its closed configuration to prevent reflux of CSF, such that only flow from the brain 24 to the amniotic sac 23 is allowed.

Figures 3A, 3B:
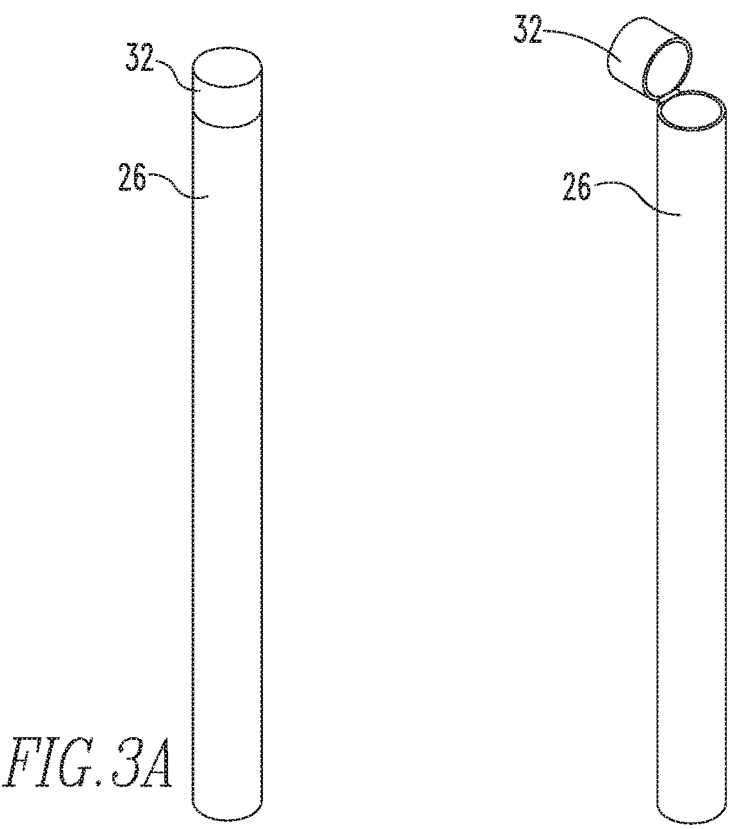
FIGS. 3A and 3B are schematics that show a detailed view of the valve shown in FIG. 2, in accordance with certain embodiments of the invention.

FIGS. 3A and 3B are schematics showing detailed views of the valve 32. FIG. 3A illustrates the closed configuration of the valve 32, such that it covers the opening of the tube 26, and FIG. 3B illustrates the open configuration of the valve 32, such that it is pushed away from the tube 26 to partially expose the opening.

It is contemplated that ventriculoamniotic shunting devices designed and developed in accordance with the invention exhibit one or more of the following performance characteristics:

Percutaneous, ultrasound-guided insertion technique to minimize maternal harm;
  Ability to anchor the shunting device to reduce potential for dislodgement;
  One-way valve mechanism to prevent reflux of amniotic fluid into the cerebral ventricles;
  Sufficiently large bore to prevent occlusion from clot or debris;
  Sufficiently small bore to prevent over-drainage of CSF;
  Capability for prolonged (e.g., about four months) drainage during fetal growth; and
  Composed of materials that are atraumatic to CNS structure (e.g., ependyma, white matter) internally and to membranes, placental vessels and myometrium externally for the duration of deployment.

It should be understood that the embodiments described herein and the examples below are for illustrative purposes only and that various modifications or changes in light thereof will be suggested to persons skilled in the art and are to be included within the spirit and purview of this application.

EXAMPLES

PEUU was prepared by a two-step polymerization process whereby polycaprolactone diol, 1,4-diisocyanatobutane, and 1,4-diaminobutane were combined in a 1:2:1 molar ratio. In the first step, a pre-polymer was formed by reacting polycaprolactone diol with 1,4-diisocyanatobutane. In the second step, the pre-polymer was reacted with 1,4-diaminobutane to extend the chain and to form the final polymer.

A PEUU coating and a PEUU valve were fabricated by electrospinning. The PEUU was dissolved in 1,1,1,3,3,3-hexafluoroisopropanol (HFIP) at a concentration of 12% (w/v), and electrospun directly onto the superelastic nitinol mesh anchor to achieve a thin layer of coating, and onto a rotating and translating stainless steel mandrel to yield a PEUU membrane. The feeding rate of the PEUU solution through a charged capillary was kept at about 1.5 ml/h, the collecting target (nitinol anchor or rotating mandrel) was located about 10 cm from the tip of the capillary, and the voltage between the capillary and target was about 19 kV.

Figure 4:
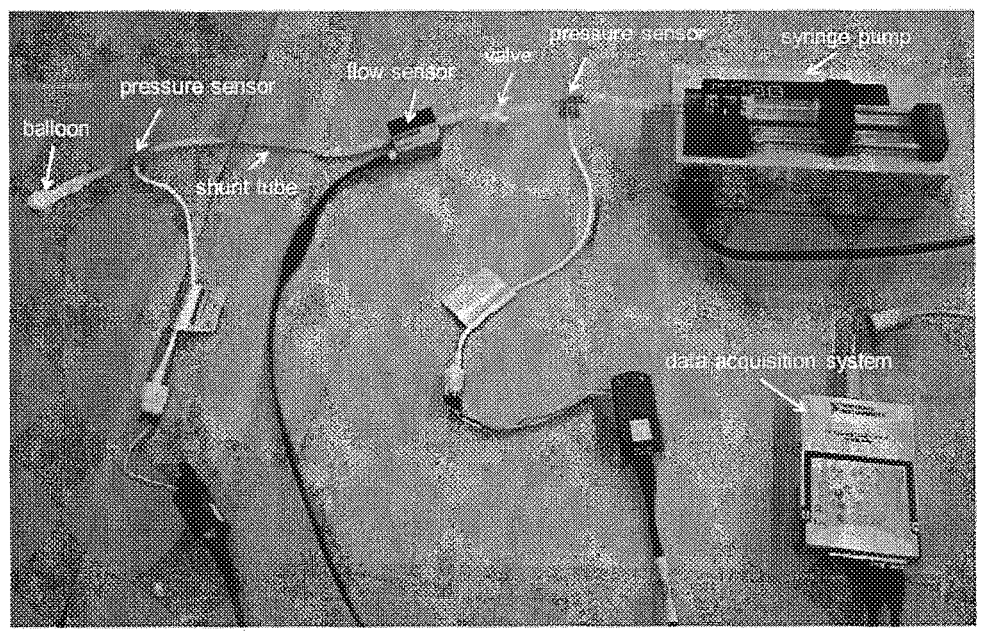
FIG. 4 is an image that shows an in vitro measurement testing set-up, in accordance with certain embodiments of the invention.

FIG. 4 shows the test set-up that was used to perform a ventriculoamniotic shunt functionality assessment. A syringe itself on a syringe pump (Model 100 Series, Cole-Parmer, IL) mimicked the fetal brain and a pump was used to mimic the pressure level increase in the fetal brain. A 3 Fr size or 4 Fr size device was connected to the test system to work as a shunt. A balloon was attached on one end of the device mimicking the amniotic sac. Two micro pressure sensors (Pendotech, NJ) were connected in a flow circuit to measure the pressure levels both in the artificial fetal brain and amniotic sac, respectively. The pressure signals were collected by a data acquisition system (NI USB-9162, National Instruments, TX) and recorded in Labview (National Instrument, TX). The flow rates in the shunt were measured by an accurate liquid flow sensor (SLI-2000, Sensirion, CA). A one-way valve between the syringe pump and the flow sensor was connected to manually control the incoming flow to the shunt and to evaluate the shunt functionality by comparing the pressure levels without and with the shunt.

It is known in the art that cerebrospinal fluid (CSF) has a viscosity similar to water. Thus, deionized (DI) water was used as the working fluid for the in vitro tests. First, the valve was closed and the pressure levels were increased in the artificial fetal brain with the pump flow rate set at 50 mL/h. This experiment mimicked the gradual pressure elevation in a fetal brain induced by CSF accumulation. Both the pressure levels in the fetal brain and amniotic sac were recorded after 7.2 s with total flow volume equal to 0.1 mL. This was marked as the control group without a shunt. Next the pressure levels were restored to the initial values. Then, the valve was turned on to mimic the shunting procedure. After all of the pressure levels were stabilized, the syringe was turned on with the same settings to mimic the pressure elevation in the fetal brain. The corresponding pressure levels and flow rates were measured and recorded. This was marked as the group with the shunt.

The anchor's functionality was evaluated by measuring the frictional force generated during shunt movement in the fetal skull. This frictional force served to prevent shunt dislocation. A 5 mm-thick polydimethylsiloxane (PDMS) membrane was fixed on an optics mount (Thorlabs, NJ), which acted as the simulating fetal skull due to similar elastic modulus. The PDMS membrane was punctured with a needle to create the incision. A vertical translation stage with maximal travel distance 13 mm (Thorlabs, NJ) was used to provide the shunt advancement through the artificial fetal skull layer and the corresponding frictional force was measured by a load cell (LSB200, Futek, CA) mounted on the translation stage.

The ventriculoamniotic shunt device contained a low-profile one-way valve fabricated by PEUU membrane. The functionality of this valve was qualitatively evaluated by visualizing the fluid flow around the valve area. The device was immersed in saline solution and then red colored food dye (Colorante rojo para alimentos, McCormick® Culinary, MD) was injected into the shunt. Both the valve motion and red dye flow in saline solution were monitored under a high resolution digital camera (NEX-3, SONY, Japan) equipped with stereomicroscopy (SZ61, Olympus, PA) at 4.5 times magnification.

Theoretical analysis and computational fluid dynamics (CFD) modeling was performed as follows.

For an incompressible flow in the circular tube, the pressure drop was calculated by the Darcy-Weisbach equation:

$$\Delta P = f_D \cdot \frac{L}{D} \cdot \frac{\rho v^2}{2} \quad (1)$$

where $f_D$ is Darcy friction factor, L and D is the length and diameter of the tube, $\rho$ is the fluid density and v is the mean flow velocity of the liquid.

For the laminar flow in a circular pipe, Darcy friction factor $f_D$ is given by:

$$f_D = \frac{64}{Re} \quad (2)$$

where Re is Reynolds number, defined as $$Re = \frac{\rho v D}{\mu}, \rho$$

is the fluid density, v is the mean flow velocity, and $\mu$ is the dynamic viscosity of the fluid.

Therefore, the volume flow rate Q was expressed as:

$$Q = \frac{\Delta P \cdot \pi D^4}{128 \mu L} \quad (3)$$

For the turbulent flow with Reynolds number greater than 4000, the Darcy friction factor $f_D$ is given by:

$$1/\sqrt{f} = -2 \log_{10}(\epsilon/3.7D + 2.51/Re\sqrt{f}) \quad (4)$$

wherein, $\epsilon$ is the roughness height.

The fetal intracranial and intrauterine pressure was known to be 30-35 mmHg and 5-9 mmHg, respectively. The pressure difference between the fetal brain and amniotic sac was estimated as 30 mmHg (~4 kPa). A simplified model was employed in CFD calculations to optimize the shunt design to maximize the flow rate in the shunt when it was connected between the fetal brain and amniotic sac. The 4 kPa pressure difference between the inlet and outlet was maintained in a cylindrical tube (shunt). The fluid in the tube was known to have the density $\rho$=1000 kg/m$^3$ and viscosity $\mu$=1.003×10$^{-4}$ Pa·s. A laminar flow model was assumed and solved for the inlet velocity, as well as flow rate for different lengths (from 3 cm to 10 cm with a 1 cm increment) and diameters (ID=0.69 mm for 3 Fr catheter and ID=0.94 mm for 4 Fr catheter).

Figure 5:
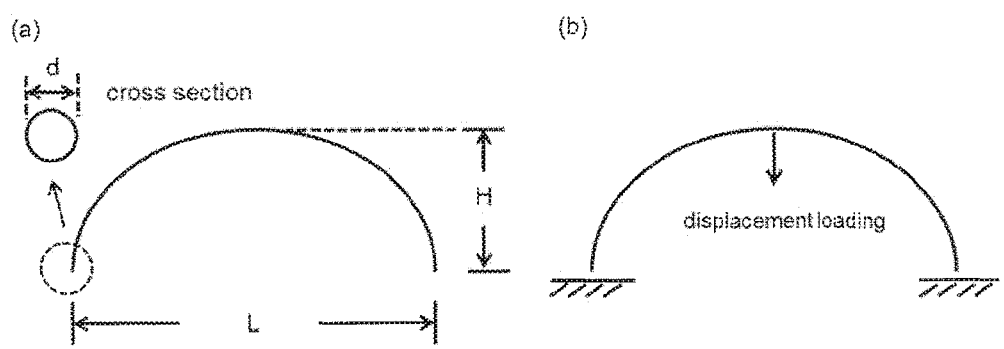
FIG. 5 is a diagram that shows a simplified model to analyze anchor resistance, in accordance with certain embodiments of the invention.

Nitinol wires with different pre-shaped structures were attached on the outer surface of the catheter as an anchor to prevent the device dislocation by generating a sufficiently high frictional force. It was assumed that the frictional force was proportional to the support force when the anchor was compressed during the device movement through the skull's incision, in order to analyze the maximal compression force in the shunt movement. A line model with circular cross section (diameter of the cross section d=0.10 mm) was employed in ANSYS Static Structural 15.0 (shown in FIG. 5). The length L (mm) and the height H (mm) of the anchor were varied to evaluate the maximum compression force. Two vortices at two ends were assumed to be fixed and a downward displacement loading with the magnitude equal to H was applied in the middle section of the anchor. The material property of the nitinol was defined as Young's Modulus E=60 GPa and Poisson's ratio v=0.3. Then the compression force associated with the displacement was evaluated.

Figure 6:
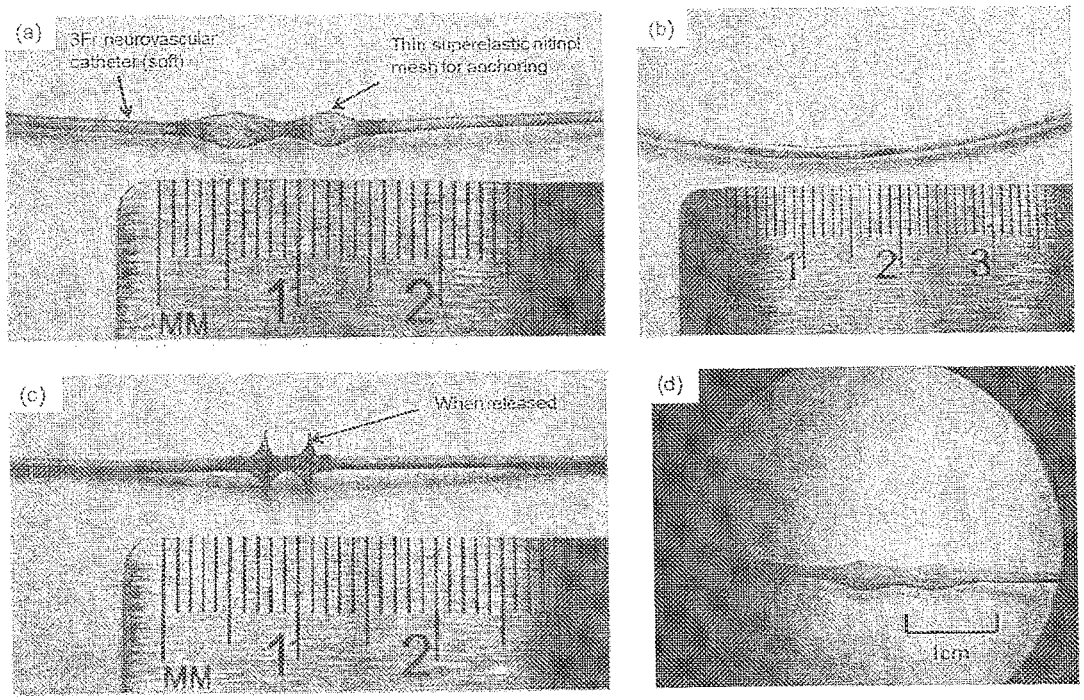
FIG. 6 is an image that shows a ventriculoamniotic shunt device, in accordance with certain embodiments of the invention.

FIG. 6 shows a shunt device with nitinol braided anchor. A commercially available catheter material (3 Fr catheter) was obtained by a precision mechanical cutting process in the pre-determined length as the shunt tube. Both ends were smoothed by eliminating any metal wires and burrs in the composite structure with mechanical polishing and micro laser melting. Then, the ultra-thin nitinol wires (0.004-0.005" diameter) were integrated with the shunt tube using both biocompatible polymer adhesives and 7-11 size nylon suturing materials (FIG. 6a). The device was easily collapsed into an ePTFE tube (Inner diameter=1.5 mm), as shown in FIG. 6b. As shown in FIG. 6c, the nitinol mesh released after compression due to the material superelasticity and prevented device dislocation by deformation. Then, all of the anchor regions were covered with PEUU membrane by an electrospun coating (FIG. 6d) to prevent any leakage of the fluid flow.

While the device was very low profile and the anchor performance was superior, there were some fluid leakage issues on the PEUU-covered region. Also, the quantity of fluid flow was not sufficient to reduce the shunt pressure rapidly and efficiently. Several other devices were manufactured with three different anchor geometries, as shown in FIGS. 1A, 1B and 1C, and tested. The anchor geometries were created with ultra-thin nitinol wires (0.004-0.005") by thermal shape setting technique. Then, the anchors were attached on the middle of the shunt tube by 7-11 size nylon suturing materials. As previously indicated, FIGS. 1A, 1B and 1C show devices with coiled spring anchors, two bumper anchors and two tilted elastic anchors, respectively. A passive one-way valve was attached on one end of the shunt tube using the micro suturing methods with the size of 10-11 sutures.

Figure 7:
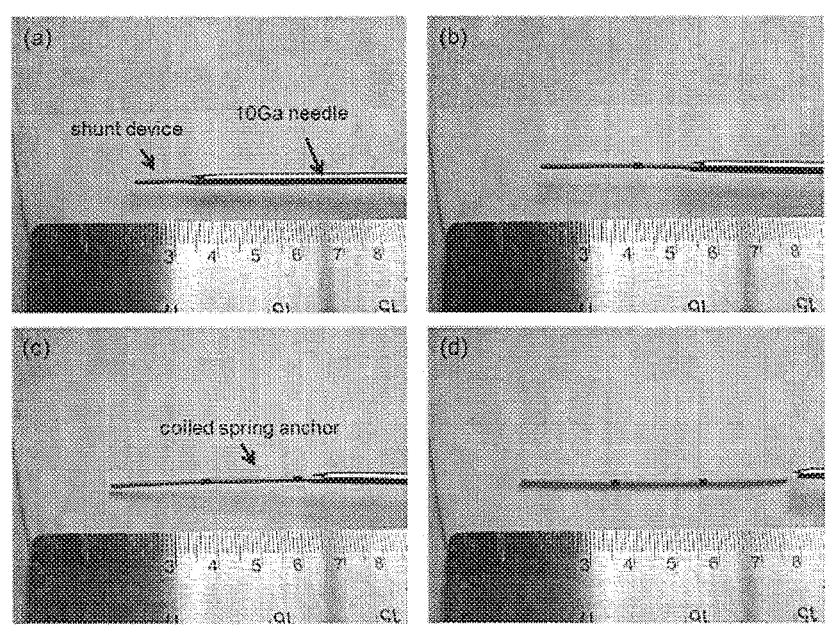
FIG. 7 is an image that shows ventriculoamniotic shunt device deployment, in accordance with certain embodiments of the invention.

FIG. 7 shows the deployment of the device in vitro. All three types of anchors, i.e., shown in FIGS. 1A, 1B and 1C, were easily collapsed and inserted into 4 Fr size shunt tubes and successfully deployed with 10 Ga needles by pushing the device using a push rod (see FIGS. 7a-7d). No significant damage or luminal side deformation was observed. The performance of the anchors was tested by deforming upon compression to demonstrate the prevention of device dislocation.

CFD calculations were performed using ANSYS Fluent 15.0. The results showed that the flow rate in a 4 Fr shunt decreased from ~1200 µL/s to ~600 µL/s when the shunt length was increased from 3 cm to 10 cm, while the flow rate in 3 Fr shunt decreased from ~450 µL/s to ~200 µL/s. Also, the 4 Fr shunt showed a larger flow rate compared to the 3 Fr shunt with the same length. Therefore, it was concluded that a catheter with larger inner diameter and smaller length was preferable for the shunt to drain a maximum amount of CSF from the brain.

The flow rate was also calculated using the theoretical equation (3). The results indicated that the flow rate in the 4 Fr shunt decreased from ~2600 µL/s to ~800 µL/s while the flow rate in the 3 Fr shunt decreased from ~800 µL/s to ~200 µL/s, when the length increased from 3 cm to 10 cm. The CFD calculation results matched with the theoretical equation calculation results. There were larger differences between the CFD and theoretical results with a smaller length for the 4 Fr catheter potentially due to calculation errors in ANSYS, since the generated mesh was not further refined with the smaller length.

A 7 cm-long 4 Fr catheter was found to minimize the surgical difficulty in practice because a shunt with a smaller length was difficult to place in the fetal skull. Also, a larger diameter of catheter needs a larger insertion needle diameter in the fetal skull, which means higher risks of premature labor, amniotic fluid leak, uterine trauma or placental separation and fetal brain trauma. Thus, 5 Fr or larger catheters were not considered for use in the shunt device.

The pressure levels and flow rates with a 3 Fr catheter (7 cm long) as the ventriculoamniotic shunt were measured. The initial pressure in the fetal brain was set as 0.86 psi and amniotic sac was 0.24 psi. Therefore, the pressure difference therebetween was 0.64 psi (32 mmHg). The pressure levels were measured in the fetal brain with the valve closed, i.e., the control group. The pressure in the fetal brain ramped to as high as 4.2 psi with the syringe pump running for 7.2 s if the shunt was not connected in the system. The pressure elevation in the fetal brain was 388%, and this high pressure represented a high risk of fetal brain damage. The pressure levels were measured in the fetal brain and amniotic sac with the valve open, i.e., the shunt was connected and functioning. It was seen that the pressure level in fetal brain first dropped to around 0.15 psi and the pressure level in amniotic sac slightly increased to around 0.25 psi when the valve was turned on. The pressure redistribution occurred between the fetal brain and amniotic sac, and the excess CSF drained from the brain to the amniotic sac. The corresponding flow rate in the shunt during this process was measured and represented by a peak value, which was 2237.2 uL/min. After all the pressure levels became stable, the pressure level in the fetal brain only increased to around 0.48 psi with the syringe pump running for 7.2 s. There was also a slight increase in the pressure level from 0.24 psi to 0.30 psi in the amniotic sac. Therefore, the pressure decrease in fetal brain was 88.6% (from 4.2 psi to 0.48 psi) while the pressure elevation in amniotic sac was 25%.

The pressure level and flow rate with 4 Fr catheter (7 cm) as the ventriculoamniotic shunt were measured. The initial pressure levels in the fetal brain and amniotic sac were set as 0.86 psi and 0.24 psi, respectively. The pressure in the fetal brain dropped suddenly to around 0.15 psi after turning on the valve. The corresponding flow rate in the shunt during this process was represented by a peak value, which was 4134.6 uL/min. This flow rate was larger than in the 3 Fr case. Then, the pressure level in the fetal brain slowly increased to approximately 0.2 psi with the syringe pump running for 7.2 s. There was also a slight increase in the pressure level from 0.24 psi to 0.29 psi. Therefore, the pressure decrease in the fetal brain was 95.2% (from 4.2 psi to 0.2 psi) and the pressure elevation in the amniotic sac was 20.8%

The pressure measurement demonstrated that the ventriculoamniotic shunt relieved the high pressure in the fetal brain with draining the excess amount of CSF to the amniotic sac. Further, pressure increase in the fetal brain was also relieved after inserting the shunt. It was seen that a 4 Fr shunt provided superior performance on CSF draining and pressure relieving. The measured peak flow rates for 3 Fr and 4 Fr shunt were much lower than the CFD calculations, primarily because the length of silicone tube in the experiment, as well as frictional loss in the tube connections, were not taken into account in the calculations. Considering all the factors, the 4 Fr catheter proved to be a suitable ventriculoamniotic shunt. It relieved 95.2% of the abnormal high pressure in fetal brain while only increasing the amniotic sac pressure by 20.8%. The actual amniotic sac size was much larger than the fetal brain, so the impact on amniotic sac was negligible.

To evaluate the effect of anchor height and length on the compression force, the anchor height was varied from 1 mm to 4 mm with fixed length L=8 mm. An asymptotic function was fit and the data revealed that increasing the anchor height elevated the generated compression force, but the improvement was not significant after the height was beyond 4 mm. Also, the anchor length was varied from 10 mm to 30 mm with fixed height H=1 mm. An exponential function was fit, which showed that decreasing the anchor length increased the generated compression force significantly. Therefore, it was concluded that an anchor design with larger height and lower length provided the optimal frictional force during the movement. However, considering the manufacturing difficulty and performance improvement, the height between 3 mm and 4 mm and length between 5 mm and 10 mm were considered as the design parameters.

This FE analysis only applied to the two bumper anchor structure in FIG. 1B, while the behaviors for coiled spring and tilted curves were more complicated since other deformations such as twisting was involved when the anchor part moved through the PDMS membrane.

Ventriculoamniotic shunts with different anchor designs were evaluated for anchor functionality. If the shunt anchor was effective in preventing the dislocation, then it would generate higher frictional force during the shunt movement in the PDMS membrane. According to this assumption, the force was measured for the coiled and tilted anchor designs shown in FIGS. 1A and 1C.

The measured force for the shunt device with coiled anchors was obtained. The frictional force when only the bare shunt (no anchor) region was pushed through the PDMS membrane was measured, and the averaged force was 0.18 N. The corresponding frictional force when the anchor region was pushed through the PDMS membrane was measured and the averaged force was 0.27 N. It shows that the presence of the anchor provided a 0.1 N frictional force to prevent the shunt dislocation during the surgery operation. For the two bumper design, the shunt anchor region first went through the PDMS membrane and the averaged frictional force was 0.15 N. Once the no-anchor region was pushed through the PDMS membrane, the frictional force abruptly ramped to 0.20 N. The frictional force on the anchor region was lower than the no anchor region, potentially due to the smoother nitinol anchor region compared to the bare catheter. Therefore, the anchor showed no effect to prevent the shunt dislocation. For the two tilted curves, the movement pattern was similar. First, the shunt anchor region was pushed through the PDMS membrane and the frictional force generated by the anchor was up to 1.0 N. After the anchor passed the PDMS membrane, the frictional force ramped down to 0.2 N. Therefore, the anchor with tilted curves provided an additional ~0.80 N frictional force to prevent shunt dislocation.

The one-way, passive valve used in the ventriculoamniotic shunt was adopted from the geometry of bi-leaflet valve. The Young's Modulus for valve material is 3 MPa with Poisson's ratio 0.49, and Young's Modulus is 1 GPa with Poisson's ratio 0.46 for catheter material. A poly(ester urethane) urea (PEUU) valve was deformed outward and pushed open with a forward flow. Further, the PEUU valve was deformed inward and remained closed with a reversed flow. Therefore, testing of the PEUU valve proved the functionality of the passive, one-way valve in allowing forward flow while resisting reversed flow.

Figure 8:
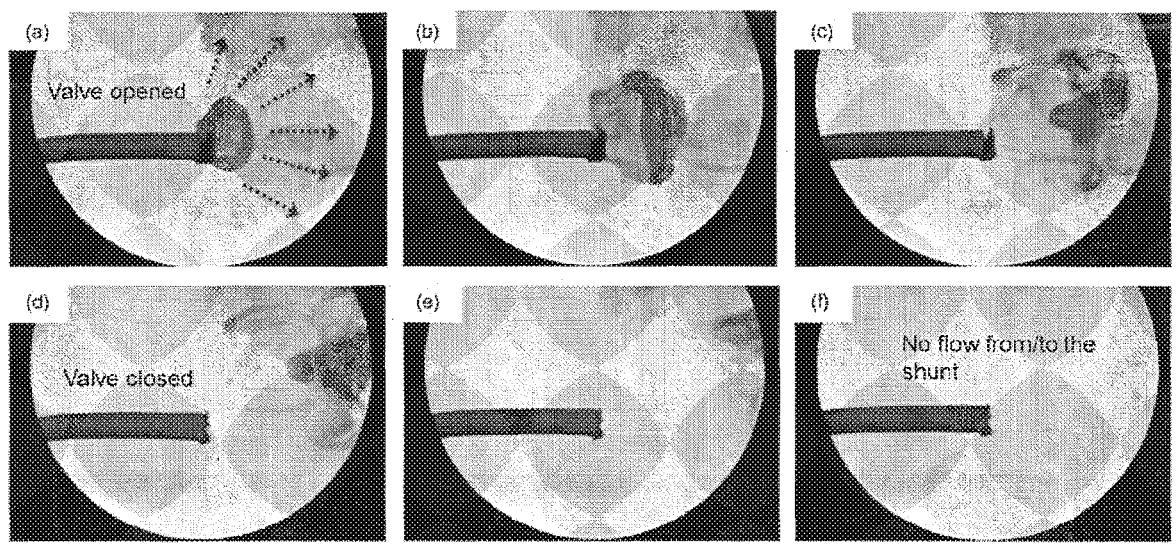
FIG. 8 is an image that shows flow visualization of a one-way valve, in accordance with certain embodiments of the invention.

FIG. 8 shows the in vitro testing results of the one-way valve with flow visualization. FIGS. 8a-8c show that injected dye into the shunt tube created high pressure and forwarded flow to push the PEUU membrane valve open. Therefore, the dye diffused into the clear DI water in all directions through the gap between the valve and end of the tube. Due to the elasticity of the PEUU membrane, the valve was restored to its original position (FIG. 8d) when the dye flow in the shunt stopped. There was no flow observed around the shunt when the valve was closed (FIGS. 8e and 8f). Thus, the valve testing confirmed the functionality of the one-way valve for controlling the flow in the shunt device.

The low-profile prototype ventriculoamniotic shunt integrated with dislodgement prevention anchors and passive one-way valve was designed and manufactured. Both 3 Fr and 4 Fr catheters served as the shunt tube and thermal shaped nitinol wires were attached on the outer tube surface to form the anchors. Finally, the PEUU membrane was attached on one end of the shunt tube as a passive one way valve. In vitro pressure level and flow rate measurement proved the shunt functionality as the 3 Fr shunt relieved 88.3%, while the 4 Fr shunt relieved 95.2% of the abnormal high pressure in the fetal brain. The measurement of frictional force generated by anchors upon compression through the simulated fetal skulls compared the anchor performance of three different designs quantitatively. The flow visualization of a passive one-way valve functionality was evaluated with flow visualization. In summary, the new ventriculoamniotic shunt device showed superior performance of draining the excess cerebrospinal fluid from the high pressurized fetal skull, reducing the likelihood of device dislodgment during the surgery operation, and preventing the reflux of amniotic fluid into the cerebral ventricles.

We claim:

1. An in-utero ventriculoamniotic shunting device, comprising:
   a shunt tube (26), comprising:
      an exterior surface;
      a first end;
      an opposite second end;
      a length;
      an inner diameter;
      an outer diameter;
      a composite that forms the inner diameter and the outer diameter, the composite comprising:
         one or more polymer layers; and
         metallic wire embedded in the one or more polymer layers;
   one or more anchors (28) mechanically attached to the exterior surface of the shunt tube (26), the one or more anchors (28) comprising:
      nitinol wire configured in a shape that extends outwardly from the exterior surface of the shunt tube (26) to prevent migration of the shunting device; and
      a mechanism (30) to connect the nitinol wire to the exterior surface of the shunt tube (26); and
   a one-way passive valve (32), comprising:
      a membrane cover mechanically connected to a portion of a perimeter of the opposite second end of the shunt tube (26) in a hinge-like configuration.

2. The device of claim 1, wherein the length of the shunt tube (26) is from about 2 to about 10 cm.

3. The device of claim 1, wherein the inner diameter of the shunt tube (26) is from about 0.5 to about 1.5 mm.

4. The device of claim 1, wherein the outer diameter of the shunt tube (26) is from about 1.0 to about 3.0 mm.

5. The device of claim 1, wherein the nitinol wire is configured in the shape of a coil (5) having a plurality of spirals formed on the exterior surface and wrapped around the outer diameter of the shunt tube (26).

6. The device of claim 1, wherein the nitinol wire is configured in the shape of two curves (10) extending outwardly from the exterior surface of the shunt tube (26).

7. The device of claim 1, wherein the one or more anchors (30) is mechanically attached to the outside surface of the shunt tube at a position approximately mid-point on the length of the tube.

8. The device of claim 1, wherein the one or more anchors (30) has a length of about 1 to about 4 cm.

9. The device of claim 1, wherein the valve (32) comprises a thin polymeric membrane.

10. The device of claim 9, wherein the valve (32) comprises poly(ester urethane) urea.

11. The device of claim 10, wherein the poly(ester urethane) urea is fabricated by electrospinning.

12. A method of ventriculoamniotic shunting for fetal isolated aqueductal stenosis, comprising:
   prenatally detecting and diagnosing aqueductal stenosis in a fetus;
   forming a shunting device, comprising:
      obtaining a shunt tube (26), comprising:
         an exterior surface;
         a first end having an opening;
         an opposite second end having an opening;
         a length;
         an inner diameter;
         an outer diameter;
         a composite that forms the inner diameter and the outer diameter, the composite comprising:
            one or more polymer layers; and
            metallic wire embedded in the one or more polymer layers;
      mechanically attaching one or more anchors (28) to the exterior surface of the shunt tube (26), comprising:
         fabricating nitinol wire;
         thermally configuring the nitinol wire in a shape that extends outwardly from the exterior surface of the shunt tube (26) for preventing migration of the shunting device; and employing a mechanism (30) for connecting the nitinol wire to the exterior surface of the shunt tube (26); and mechanically attaching a membrane cover (32) to a portion of a perimeter of the opposite second end of the shunt tube (26) in a hinge-like configuration;

introducing the shunting device in-utero through a skull (22) and into a brain (24) of the fetus, such that the first end of the shunt tube (26) is positioned in the skull (22) and the opposite second end of the shunt tube (26) is positioned in an amniotic sac (23) outside of the skull (22);

allowing cerebrospinal fluid in the brain (24) to flow into the first end and through the shunt tube (26);

pushing outward the membrane cover (32) by the flow of cerebrospinal fluid through the shunt tube (26); and discharging the cerebrospinal fluid through the opposite second end of the tube (26) into the amniotic sac (23).

\* \* \* \* \*